United States Patent [19]
Sutton et al.

[11] Patent Number: 5,397,695
[45] Date of Patent: Mar. 14, 1995

[54] ATTACHMENT OF COMPOUNDS TO POLYMERIC PARTICLES USING CARBAMOYLONIUM COMPOUNDS AND A KIT CONTAINING SAME

[75] Inventors: Richard C. Sutton, Irondequoit; Susan J. Danielson, Rochester; Pranab Bagchi, Webster; Patricia M. Scensny, Rochester, all of N.Y.

[73] Assignee: Eastman Kodak Company, Rochester, N.Y.

[21] Appl. No.: 373,304

[22] Filed: Jun. 29, 1989

Related U.S. Application Data

[63] Continuation-in-part of Ser. No. 286,097, Dec. 19, 1988, abandoned, which is a continuation-in-part of Ser. No. 98,249, Sep. 18, 1987, abandoned.

[51] Int. Cl.$^6$ .................. C12Q 1/70; G01N 33/543; C07K 3/00; C12N 11/08
[52] U.S. Cl. .................................. 435/5; 435/292; 435/180; 435/181; 435/810; 435/975; 436/518; 436/523; 436/528; 436/531; 436/532; 530/300; 530/350; 530/387.1; 930/200; 930/220
[58] Field of Search ................. 435/5, 7.92, 180, 181, 435/810, 975; 430/422; 436/518, 523, 528, 531, 532; 530/300, 350, 387.1; 930/200, 220

[56] References Cited

U.S. PATENT DOCUMENTS

| | | | |
|---|---|---|---|
| 4,119,464 | 10/1978 | Sauerteig et al. | 96/68 |
| 4,659,678 | 4/1987 | Forrest et al. | 436/512 |
| 5,053,443 | 10/1991 | Sutton | 523/332 |

OTHER PUBLICATIONS

Pierce Immuno Technology Catalog & Handbook, p. E12.
*Microparticle Immunoassay Techniques*, 2nd Ed., Seradyn, Inc. 1988.
Weingard et al. Cancer Res. 45(8), 1985, 3529–3536 abstract only.

*Primary Examiner*—Margaret Parr
*Assistant Examiner*—Bradley L. Sisson
*Attorney, Agent, or Firm*—J. Lanny Tucker

[57] ABSTRACT

Useful materials for diagnostic tests, affinity chromatography, enzymatic reactions and immunoassays are prepared by covalently attaching reactive compounds containing reactive amino or sulfhydryl groups to polymeric particles having pendant carboxyl groups on the outer surfaces. Such reactive compounds include biologically reactive species, such as enzymes, polypeptides and proteins. This attachment is carried out using carbamoylonium compounds which react with the carboxyl groups to form intermediate reactive groups which then react with the amino or sulfhydryl groups to form a covalent linkage between particle and reactive compound. A kit comprises polymeric particles having carboxyl groups on the outer surfaces, and a carbamoylonium compound.

27 Claims, No Drawings

ATTACHMENT OF COMPOUNDS TO POLYMERIC PARTICLES USING CARBAMOYLONIUM COMPOUNDS AND A KIT CONTAINING SAME

REFERENCE TO RELATED APPLICATION

This application is a continuation-in-part of U.S. Ser. No. 286,097, filed Dec. 19, 1988, abandoned, which in turn is a continuation-of-part of U.S. Ser. No. 098,249, filed Sep.18, 1987 (now abandoned).

FIELD OF THE INVENTION

The present invention relates to a method for the preparation of polymeric particles having compounds attached thereto. In particular, it relates to the preparation of such materials by attachment of reactive amine- or sulfhydryl-containing compounds to polymeric particles using carbamoylonium compounds. It also relates to a kit comprising polymeric particles and a carbamoylonium compound.

BACKGROUND OF THE INVENTION

Biologically active polypeptides or proteins which are attached to insoluble carrier materials, such as polymeric particles, have been used in a variety of ways. For example, the diagnosis of pathological or other conditions in human beings and animals is often carried out using immunological principles for the detection of an immunologically reactive species, for example antibodies or an antisen, in the body fluids of the person or animal. An antigen is generally known as a foreign substance, such as a drug, hapten, toxin, lectin, polypeptide or protein which, when introduced into the body, causes the production of certain soluble proteins known as antibodies.

Other proteins and amine-containing compounds, such as enzymes, avidin, biotin or polysaccharides, have been covalently linked to various carrier materials for use in affinity chromatography, enzymatic reactions, specific binding reactions and immunoassays. Among useful carrier materials are sheep and human erythrocytes, bacterial cells, latex particles, resinous particles and finely divided diazotized amino cellulose. For example, carrier particles prepared from sparingly water-soluble monomers (such as epoxy group-containing monomers) in the absence of emulsifiers are described in U.S. Pat. No. 4,415,700 (issued Nov. 15, 1983 to Batz et al). Other compounds, such as diamines, dihydrazides, mercaptoalkylamines and dimercaptans have been attached to carrier materials as linking moieties for later attachment of drugs, enzymes or other reactive species.

Carboxylated latex particles have also been used to prepare diagnostic reagents as described, for example, in U.S. Pat. No. 4,181,636 (issued Jan. 1, 1980 to Fischer). As described therein, the conventional procedure for covalently attaching an immunologically reactive species to the particles having surface carboxyl groups involves the use of a water-soluble carbodiimide. While producing useful reagents, this procedure tends to activate the exposed reactive groups of the reactive species as well as the carboxyl groups. The result is intramolecular and intermolecular crosslinking or polymerization of the immunologically reactive species, and a significant portion of the species is thus impaired from complexation with a receptor molecule. Because the reactive species, for example an antibody, is usually very costly, this problem represents a serious economic loss. It has also been evident that the use of carbodiimides to attach proteins to carrier particles is not as efficient as desired at certain protein levels.

It would be desirable to have a rapid method for attaching a reactive amine-containing compound to carboxylated polymeric particles in an efficient manner and without adversely affecting the attached compound.

SUMMARY OF THE INVENTION

The problems noted above are overcome with a method for attaching a reactive amine- or sulfhydryl-containing compound to polymeric particles comprising A. contacting (1) an aqueous suspension of polymeric particles having pendant carboxyl groups on the surface thereof with (2) a carbamoylonium compound to produce reactive intermediate polymer particles having pendant intermediate reactive groups, and B. contacting the reactive intermediate polymer particles produced in step A with a reactive amine- or sulfhydryl-containing compound having a reactive amino or sulfhydryl group, respectively, which reacts with the intermediate reactive groups to form a covalent linkage between the particles and the reactive compound.

This invention also provides a kit comprising: (1) polymeric particles having pendant carboxyl groups on the surface thereof,and (2) a carbamoylonium compound.

The present invention provides a means for rapidly attaching a reactive amine- or sulfhydryl-containing compound, such as a biologically active polypeptide or protein to insoluble polymeric particles, thereby forming useful materials for immuno-assays, diagnostic tests, affinity chromatography, enzymatic reactions and other biological or chemical procedures. The attachment is achieved without adversely affecting the reactive compound which is attached. That is, there is minimal crosslinking or deactivation of the reactive amino or sulfhydryl groups in the reactive compound which participate in the formation of a covalent linkage with pendant carboxyl groups of the particles.

These advantages are achieved by using a particular class of attachment agents. These agents are carbamoylonium compounds which have not been heretofore used for this purpose. It was initially expected that such compounds, like the conventional carbodiimides, would indiscriminately deactivate the reactive amine or sulfhydryl groups of the reactive compounds. Unexpectedly, we found this not to be the case, and thereby discovered the very useful and efficient attachment method described and claimed herein.

DETAILED DESCRIPTION OF THE INVENTION

The materials prepared according to the method of the present invention can be used in many different chemical and biological procedures. For example, they can be used in affinity chromatography, reactions catalyzed by enzymes, water purification, immunoassays wherein the analyte is an immunologically reactive species which has specific binding affinity for an attached polypeptide or protein, and other processes known to one of ordinary skill in the art. In some instances, the present invention can be used to attach intermediate linking moieties which can be further reacted with compounds of biological interest, such as drugs, hormones, enzymes, antibodies or other proteins or polysaccharides.

One use of the materials prepared by the present invention is as an agglutination immuno-chemical reagent in an agglutination assay wherein the analyte or material to be detected is an immunologically reactive species found in physiological fluids, cells or tissue extracts of humans or animals, for which an immunological counterpart (or receptor) is available or can be produced. Representative immunologically reactive species for which the reagent can be used to detect include, but are not limited to, microorganisms (bacteria, protozoa, fungi, viruses and rickettsia), tissue antigens including organ specific antigens, hormones, enzymes, blood cell antigens or other substances found in the blood, plasma proteins, milk proteins, saliva proteins, urine proteins, pathologic proteins, antibodies including autoantibodies and drugs. In such instances, the reactive amine- or sulfhydryl-containing compound used in the method of this invention is an immunological compound which is a receptor for the analyte of interest, for example an antigen or antibody.

In other embodiments, the material described herein can have an enzyme attached to the particles. Enzymes which can be attached in this manner include those which have reactive amine or sulfhydryl groups which can be reacted according to the present invention with the active pendant groups on the particles without losing enzymatic activity.

In still other embodiments, the material prepared by this invention can be used in competitive binding assays in either a solution or dry format (that is, a dry analytical element), or in what a known in the art as immunometric assays, for example "sandwich" assays.

The method of this invention is a two-step process involving attaching a reactive amine- or sulfhydryl-containing compound which has a reactive amine or sulfhydryl group, respectively, to polymeric particles having outer surface reactive carboxyl groups using a carbamoylonium compound.

The polymeric particles useful in the method of this invention are generally water-insoluble particles having a particle size in the range of from about 0.01 to about 100 micrometers, and preferably from about 0.1 to about 3 micrometers. They can be homogeneous polymeric particles meaning that they are composed of the same polymer throughout, or they can be particles composed of more than one polymer such as graft copolymers as described, for example, in U.S. Pat. No. 3,700,609 (issued Oct. 24, 1972 to Tregear et al) and core-shell polymers described for example in U.S. Pat. No. 4,401,765 (issued Aug. 30, 1983 to Craig et al). It is critical that the polymeric particles have surface carboxyl groups available for attachment of the reactive amine- or sulfhydryl-containing compound. Such groups are preferably added to the particles by incorporating monomers containing such groups into the polymers (for example, acrylic acid, methacrylic acid, itaconic acid, and the like). Alternatively, they can be added to the particles by further chemical reaction of a polymer having other precursor reactive groups which can be converted to carboxyl groups (for example, by hydrolysis of anhydrides, such as maleic anhydride, or by oxidation of surface methylol or aldehyde end groups).

Generally, useful polymeric particles can be prepared using any suitable polymerization technique, including emulsion (including batch, semi-continuous and continuous) and suspension polymerization techniques, graft copolymerization, and others known to one skilled in the polymer chemistry art. Emulsion polymerization is preferred as it can be used to provide generally smaller particles without the use of surfactants or emulsifiers, as described for example in U.S. Pat. No. 4,415,700 (noted above) and *Research Disclosure* publication 15963 (July, 1977). *Research Disclosure* is a publication available from Kenneth Mason Publications, Ltd., The Old Harbourmaster's, 8 North Street, Emsworth, Hampshire P010 7DD, England. Continuous emulsion polymerization is the most preferred technique, as described in the noted *Research Disclosure* publication.

Useful carboxylated particles are prepared from carboxylated styrene and its derivatives, carboxylated styrene-butadiene copolymers, acrylic and methacrylic acid polymers and other materials, many of which are commercially available.

Preferably, the polymeric particles are composed of a polymer represented by the structure:

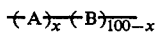

wherein A represents recurring units derived from one or more ethylenically unsaturated polymerizable monomers containing carboxylic acid groups or salts or precursors of said groups, and B represents recurring units derived from one or more ethylenically unsaturated polymerizable monomers.

Monomers from which A can be derived include, but are not limited to, acrylic and methacrylic acids, itaconic acid, aconitic acid, fumaric acid, maleic acid, $\beta$-carboxyethyl acrylate, $\beta$-carboxyethyl methacrylate, m&p-carboxymethylstyrene, methacrylamidohexanoic acid and N-(2-carboxy-1,1-dimethylethyl)acrylamide or a salt or anhydride precursor thereof. Acrylic and methacylic acids, iraconic acid, aconitic acid, fumaric acid, maleic acid, $\beta$-carboxyethyl acrylate, $\beta$-carboxyethyl methacrylate or a salt or anhydride precursor thereof are preferred in the practice of this invention. Monomers from which B can be derived include, but are not limited to, styrene and styrene derivatives (for example vinyltoluene, 4-t-butylstyrene, divinylbenzene and 2-chloromethylstyrene), acrylic and methacrylic acid esters (for example, methyl acrylate, ethyl methacylate, n-butyl acrylate, 2-ethylhexyl methacrylate, methyl methacrylate, 2-hydroxyethyl methacrylate, methacrylamide, ethylene dimethacrylate and 2-hydroxyethyl acrylate), sodium 2-acrylamido-2-methylpropoansulfonate, sodium 3-acryloyloxypropanesulfonate, p-styrenesulfonate, or acrylonitrile. Preferably, B is derived from styrene or a styrene derivative, or an acrylic or methacrylic acid ester.

For both the A and B monomers, it is important that the specific monomers used and their proportions be chosen so as to render the particles water-insoluble.

In the structure identified above, x is from about 0.1 to about 70, and preferably from about 1 to about 20, mole percent.

Representative polymers of which the polymeric particles are composed include poly-(styrene-co-vinylbenzyl chloride-co-acrylic acid) (85:10:5 molar ratio), poly(styrene-co-acrylic acid) (99:1 molar ratio), poly(styrene-co-methacrylic acid) (90:10 molar ratio), poly(styrene-co-acrylic acid-co-m&p-divinylbenzene) (89:10:1 molar ratio), poly-(styrene-co-2-carboxyethyl acrylate) (90:10 molar ratio), poly(methyl methacrylate-co-acrylic acid) (70:30 molar ratio) and poly(styrene-co-butyl acrylate-co-methacrylic acid)(45:45:10 weight ratio).

In one embodiment, the particles are core-shell particles wherein the core is composed of a first polymer, and the shell is composed of a second polymer. The second polymer must have reactive carboxyl groups or groups which can be converted to carboxyl groups prior to attachment of the polypeptide or protein. A representative example of core-shell polymeric particles is provided in Example 2 below.

The polymeric particles described herein can be supplied as a dried powder which can be resuspended for any use of interest. Preferably, however, they are supplied as an aqueous suspension generally having from about 0.1 to about 35 percent solids. Suspending agents, buffers or other addenda can be included in the suspension if desired.

Carbamoylonium salts are used for covalent attachment of the reactive amine- or sulfhydryl-containing compound to the polymeric particles in the practice of this invention. These salts are described in some detail in U.S. Pat. No. 4,421,847 (issued Dec. 20, 1983 to Jung et al), and are generally represented by the structure:

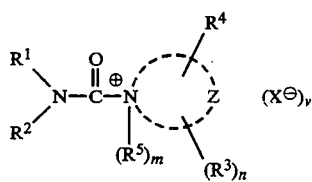
(I)

In structure (I), Z represents the atoms necessary to complete a substituted or unsubstituted 5- or 6-membered heterocyclic aromatic ring including heterocyclic rings having a fused carbocyclic ring (for example a pyridinium, imidazolium, thiazolium, isoxazolium or quinolinium ring). Preferably, Z represents the atoms necessary to complete a substituted 6-membered heterocyclic aromatic ring.

Further, m and n are independently 0 or 1, $R^1$ and $R^2$ are, independently of each other, substituted or unsubstituted alkyl (generally of 1 to 6 carbon atoms, for example, methyl, ethyl, isopropyl or chloromethyl) or substituted or unsubstituted aryl (generally of 6 to 10 carbon atoms, for example phenyl, p-methylphenyl, m-chlorophenyl or naphthyl), or substituted or unsubstituted aralkyl (generally of 7 to 12 carbon atoms, for example benzyl or phenethyl which can be substituted in the same manner as the aryl group).

Alternatively, $R^1$ and $R^2$ together represent the atoms necessary to complete a piperidine, piperazine or morpholine ring, which ring can be substituted for example with one or more alkyl groups each having 1 to 3 carbon atoms or by a halo atom.

$R^3$ is a hydrogen atom, a substituted or unsubstituted alkyl as defined above for $R^1$, or the group [A] wherein A represents the polymerized vinyl backbone of a homo- or copolymer formed from one or more ethylenically unsaturated polymerizable compounds such that the molecular weight of the homo- or copolymer is greater than about 1000. Useful ethylenically unsaturated polymerizable compounds are known to one of ordinary skill in the polymer chemistry art. The polymer [A] can comprise additional moieties derived from the compounds represented by structure (I).

$R^4$ is a hydrogen atom, a substituted or unsubstituted alkyl (as defined above for $R^1$), or when Z represents the atoms necessary to complete a pyridinium ring and n is 0, $R^4$ is selected from the following groups:

(a) —$NR^6$—CO—$R^7$ wherein $R^6$ is hydrogen or substituted or unsubstituted alkyl (generally of 1 to 4 carbon atoms, for example methyl ethyl, n-butyl, chloromethyl), $R^7$ is hydrogen, substituted or unsubstituted alkyl (as defined above for $R^6$) or —$NR^8R^9$ wherein $R^8$ and $R^9$ are independently of each other hydrogen or substituted or unsubstituted alkyl (as defined above for $R^6$), (b) —$(CH_2)_q$—$NR^{10}R^{11}$ wherein $R^{10}$ is —CO—$R^{12}$, $R^{11}$ is hydrogen or substituted or unsubstituted alkyl (as defined above for $R^6$), $R^{12}$ is hydrogen, substituted or unsubstituted alkyl (as defined above for $R^6$) or —$NR^{13}R^{14}$ wherein $R^{13}$ is substituted or unsubstituted alkyl (as defined above for $R^6$) or substituted or unsubstituted aryl (as defined above for $R^1$), $R^{14}$ is hydrogen, substituted or unsubstituted alkyl (as defined above for $R^6$) or substituted or unsubstituted aryl (as defined for $R^1$), and q is 1 to 3, (c) —$(CH_2)_r$—$CONR^{15}R^{16}$ wherein $R^{15}$ is hydrogen, substituted or unsubstituted alkyl (as defined above for $R^6$) or substituted or unsubstituted aryl (as defined above for $R^1$), $R^{16}$ is hydrogen or substituted or unsubstituted alkyl (as defined above for $R^6$), or $R^{15}$ and $R^{16}$ together represent the atoms necessary to complete a 5- or 6-membered aliphatic ring, and r is 0 to 3,

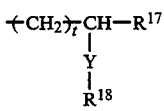

wherein $R^{17}$ is hydrogen, substituted or unsubstituted alkyl (as defined above for $R^6$), Y is oxy or —$NR^{19}$—, $R^{18}$ is hydrogen, substituted or unsubstituted alkyl (as defined above for $R^6$), —CO—$R^{20}$ or —CO—$NHR^{21}$ wherein $R^{19}$, $R^{20}$ and $R^{21}$ are independently of each other hydrogen or substituted or unsubstituted alkyl (as defined above for $R^6$), and t is 2 or 3, and (e) —$R^{21}X'^{\ominus}$ wherein $R^{21}$ is substituted or unsubstituted alkylene of from 1 to 6 carbon atoms (for example, methylene, trimethylene or isopropylene), and $X'^{\ominus}$ is a covalently bonded anionic group such as sulfonate or carboxylate so as to form an inner salt group with the pyridinium nucleus.

$R^5$ is substituted or unsubstituted alkyl (as defined above for $R^6$), substituted or unsubstituted aryl (as defined above for $R^1$) or substituted or unsubstituted aralkyl (as defined above for $R^1$), provided that m is 0 when the nitrogen atom to which $R^5$ is bound is attached to the remainder of the ring through a double bond.

X is an anion, such as a halide, tetrafluoroborate, nitrate, sulfate, p-toluenesulfonate, perchlorate, methosulfate or hydroxide, and v is 0 or 1, provided that it is 0 only when $R^4$ is —$R^{21}X'^{\ominus}$.

Preferably, the carbamoylonium compound used in the practice of this invention is represented by the structure above wherein $R^1$ and $R^2$ together represent the atoms necessary to complete a morpholine ring, Z represents the atoms necessary to complete a pyridinium ring, $R^4$ is —$R^{21}X'^{\ominus}$ (such as —$CH_2CH_2SO_3^-$), and m, n and v are each 0.

Representative carbamoylonium compounds include 1-(4-morpholinocarbonyl)-4-(2-sulfoethyl)-pyridinium hydroxide, inner salt, and 1-(4-morpholinocarbonyl)-pyridinium chloride.

Most preferred is 1-(4-morpholinocarbonyl)-4-(2-sulfoethyl)pyridinium hydroxide, inner salt.

The carbamoylonium compounds useful in the practice of this invention can be obtained commercially, or prepared using known procedures and starting materials, as described in U.S. Pat. No. 4,421,847 (noted above), and references noted therein, incorporated herein by reference.

Any reactive amine- or sulfhydryl-containing compound can be attached to polymeric particles according to the present invention as long as that compound contains a reactive amine or sulfhydryl group, respectively, which will react with the intermediate formed by the reaction of the carbamoylonium compound with carboxyl groups on the particles. Such compounds include, but are not limited to, monoamines, monohydrazides, diamines, dihydrazides, enzymes, biotin or derivatives thereof, avidin or derivatives thereof, amino acids, peptides, polypeptides, proteins, polysaccharides, and others which would be apparent to one skilled in the art. In certain embodiments, the reactive amine- or sulfhydryl-containing compound is a polypeptide or protein which is biologically active. The term "biologically active" refers to its capacity for interaction with another component which may be found in physiological fluids. Such an interaction can be catalytic activity in the case where the material is an enzyme. In addition, the interaction can be a complexation which occurs between materials which have affinity for one another, such as avidin with biotin or antibodies with antigens, and the like. In other embodiments, the reactive amine- or sulfhydryl-containing compound is a diamine, polysaccharide, amino acid, peptide or protein which can be a linking moiety for attaching a second compound to the particle. Such second compounds include, but are not limited to, enzymes, antibodies, antigens, drugs, biotin or derivatives thereof and others readily apparent to one skilled in the art.

Preferably, the reactive amine- or sulfhydryl-containing compound is an immunologically reactive species, including but not limited to the biological and chemical compounds listed above. More preferably, it is an antibody, such as an antibody directed against a drug, hormone, Streptococcus A antigen, a chlamydial antigen, a gonococcal antigen, human chorionic gonadotropin, human leutinizing hormone or a herpes virus. Alternatively, the immunologically reactive species can be an antigen, such as an antigen of HTLV-I or HIV-I.

In certain embodiments, the materials prepared by the method of this invention can have a tracer associated therewith. A tracer is a detectable species which enables one to detect the reagent. Useful tracers include radioisotopes, colorimetric or fluorometric compounds, enzymes, chemiluminescent compounds, phosphorescent compounds and others known to one skilled in the art. Particularly useful tracers are colorimetric and fluorometric compounds. The tracer can be associated with the reagent in any suitable manner. For example, the tracer can be associated (for example, covalently or ionically attached) with the biologically active polypeptide or protein. Alternatively and preferably, the tracer is associated with the polymeric particles, for example attached (covalently or adsorbed) to their outer surface or internally distributed in part or all of the volume, or both.

It is particularly desirable to incorporate tracers such as colorimetric or fluorometric dyes into the particles. Such incorporation can be accomplished by polymerizing monomers having dye or dye precursor moieties attached to the polymerizable vinyl group. Preferably, however, the dyes are "loaded" into the particles after their formation using known procedures noted below.

Particularly useful tracers which can be incorporated into particles include cyan, yellow and magenta dyes, europium and other rare earth chelates (such as a mixture of europium-thenoyl trifluoroacetonate and trioctylphosphine oxide), fluoroescent dyes such as 2,5-bis(6-butyl-2-benzoxazolyl)thiophene and 3-(2-benzothiazolyl)-7-diethylaminocoumarin and others known in the art. Incorporation of dyes can be achieved using the techniques described in U.S. Pat. No. 4,199,363 (issued Apr. 22, 1980 to Chen) and in copending and commonly assigned U.S. Ser. No. 136,214, filed Dec. 18, 1987 by Sutton, both incorporated herein by reference.

The method of the present invention is carried out in two steps, the first of which involves contacting an aqueous suspension of the polymeric particles described above with a carbamoylonium compound described above to produce reactive intermediate polymer particles having intermediate reactive groups in place of the carboxyl groups. This step is carried out at a suitable pH using suitable acids or buffers to provide the desired pH. Generally, the pH is less than 6, but this is not critical as long as the reaction can proceed. More likely, the pH is between about 3.5 and about 6. The molar ratio of carbamoylonium compound to the total measured carboxylic acid level in the polymer particles is from about 1:1 to about 200:1, and preferably from about 10:1 to about 100:1.

In the second step of the method, the reactive intermediate formed in the first step is contacted with a reactive amine- or sulfhydryl-containing compound having a reactive amine or sulfhydryl group, respectively, which will react with the intermediate reactive group of the reactive intermediate. A covalent linkage is thereby formed between the particles and the reactive compound. The weight ratio of the reactive compound to the polymeric particles is generally from about 1:1000 to about 2:1, and preferably from about 1:100 to about 1:1.

This second step can be carried out at a suitable pH such that the desired reaction occurs without premature agglutination. The pH may be varied depending upon the reactants involved and their concentration in the reaction medium. For many proteins and polypeptides, this pH will be greater than 6.

The method of the invention is generally carried out at a temperature of from about 10 to about 60° C., and preferably from about 15 to about 30° C. The temperature can be the same or different for the two steps of the method.

Further details regarding the method of this invention would be readily apparent to one of ordinary skill in the art from the representative examples described below.

The polymeric particles described above can be provided in a kit which also includes one or more carbamoylonium compounds as described herein. The particles can be free of tracer, or have a tracer associated therewith. Useful tracers are noted above, but preferred tracers include colorimetric and fluorometric dyes which have been incorporated into the particles in a suitable manner. The particles can be supplied as a powder as long as it can be resuspended for any use of interest. Preferably, they are supplied as an aqueous suspension as described above.

Such kits can optionally include a compound having reactive amine or sulfhydryl groups for attachment to the polymeric particles in the method of this invention. Other optional materials include pipettes, test tubes, instructions, buffers or other reagents and equipment which may be helpful in the practice of the invention.

EXAMPLE 1

Attachment of Protein to Poly(Styrene-co-Vinylbenzyl Chloride-co-Acrylic Acid) Particles A solution of 5.29 g (0.00932 mole) of the carbamoylonium compound 1-(4-morpholinocarbonyl)-4-(2-sulfoethyl)pyridinium hydroxide, inner salt, in 45.71 g of distilled water was added to 50 ml of a 4% suspension (pH 3.6) of poly(styrene-co-vinylbenzyl chloride-co-acrylic acid) (molar ratio 85:10:5) particles (average size of about 0.66 micrometer). The resultant mixture had a pH of about 5.0.

A portion of the activated latex containing 100 mg of polymer (dry weight) was incubated at room temperature (about 22° C.) for one hour and a second sample of the same size was incubated three hours. Each was treated with 5 mg of labeled (tritiated) bovine gamma globulin ($^3$H BGG) and brought to a final volume of 30 ml with 0.1 molar potassium phosphate (pH 7.0) in 50 ml centrifuge tubes. The reactions were continued for five hours at room temperature with end-over-end rotation at 30–35 rpm while attached to a rotating plate mounted at a 45° angle.

A control mixture (Control 1) was similarly prepared by incubating the same amount of a batch of poly(styrene-co-vinylbenzyl chloride-co-acrylic acid) (85:10:5 molar ratio) particles exactly as described above, except it had not been activated with the carbamoylonium compound, to test for nonspecific binding (adsorption). It is known from previous experiments that at low temperatures, there is little, if any, covalent bonding of the bovine gamma globulin protein to the polymer particles via the alternate reaction of the amine groups on the protein with the active chloromethyl groups on the polymer. This latter reaction requires heat and extended reaction times to proceed efficiently.

A second control mixture (Control 2) was prepared by treating 100 mg (dry weight) of latex which had not been activated with the carbamoylonium compound with 5 mg tritiated bovine gamma globulin in 30 ml 0.1 molar sodium borate buffer (pH 8.5), with end-over-end rotation as described above for 24 hours at 37° C.

At the end of the described incubation times, the reaction was quenched by addition of excess bovine serum albumin (100 mg, 20 mg/ml in the appropriate buffer). The samples were incubated another 4–18 hours after addition of the albumin.

The total amount of protein bound to the particles was determined by measuring: a) the total cpm (counts per minute) in a 1 ml aliquot of the reaction mixture, b) the cpm remaining in the supernatant following centrifugation of a 1 ml sample of the reaction mixture and c) the cpm of the latex reagent following repeated washes of the pellet obtained in b. The fraction of the protein which is covalently bound to the particles was determined following incubation of the reagents in the presence of 1% sodium dodecylsulfate surfactant at 37° C. for about 24 hours with end-over-end rotation. The same procedure described above for determining the total amount of bound protein was used to determine the amount of protein covalently bound. The results are reported in the following Tables I and II.

TABLE I

| Sample | Carbamoylonium Reaction Time | % Bound | mg protein/g Polymer |
|---|---|---|---|
| 1 | 1 Hour | 37 | 18 |
| 2 (Control 1) | None | 4 | 2 |
| 3 | 3 Hours | 36 | 18 |
| 4 (Control 2) | None | 22 | 11 |

TABLE II

| | After Surfactant Treatment | |
|---|---|---|
| Sample | % Bound | mg protein/g Polymer |
| 1 | 28 | 14 |
| 2 (Control 1) | 3 | 2 |
| 3 | 27 | 13 |
| 4 (Control 2) | 16 | 8 |

This example demonstrates that bovine gamma globulin can be covalently bound to carboxylated beads using ambient reaction conditions with fast reaction times compared to the alternative reaction schemes of Controls 1 and 2 with better binding efficiency.

EXAMPLE 2

Preparation and Use of Reagent

Two monoclonal anti-theophylline antibodies were reacted with both carboxylated polymeric particles which had been activated with the carbamoylonium compound used in Example 1 and with particles containing chloromethylstyrene functional groups. The antibodies employed were (1) monoclonal antibodies to theophylline sold by Kallested Laboratories, Inc. (Catalog No. 046, Lot No. W0729, Fill No. W0854, clone number 9-49-7A, A8), and (2) monoclonal antibodies specific for theophylline prepared by fusion of SP2/0-Ag14 myeloma cells with splenic lymphocytes from female Balb/C mice immunized with theophylline-bovine serum albumin and which are $\gamma_2$b, kappa isotype having a Ka of approximately $5 \times 10^7 M^{-1}$ in phosphate buffered saline at room temperature. The amount of antibody bound to the particles was determined in a parallel experiment in which $^3$H bovine gamma globulin was substituted for the anti-theophylline antibody. The amount of active antibody bound to the particles was compared in the enzyme label binding experiment described below.

Carboxylated latex poly(styrene-co-acrylic acid) (99:1 molar ratio) particles were activated with the carbamoylonium compound by suspending a latex containing 500 mg of polymer (dry weight) and 250 mg carbamoylonium compound dissolved in 10 ml deionized distilled water in 50 ml distilled water at a pH of 5. The latex was stirred for 30 minutes at room temperature and centrifuged. The supernatant was discarded and the latex was resuspended in about 10 ml distilled water. Separate samples of the resulting reagent (100 mg of polymer, dry weight) were mixed each with a 3.16 mg sample of one of the two types of antibodies described above in 30 ml of buffer (0.05 molar potassium phosphate, pH 7.0). The reactions were incubated with end-over-end rotation at room temperature for about 24 hours. The reactions were stopped by the addition of bovine serum albumin (100 mg, 20 mg/mL) and the incubation was continued for about four hours. The reactions were centrifuged, the supernatants were discarded, and the latices were resuspended in 30 ml phosphate buffered saline (pH 7.4) containing 1% TRITON X-100 nonionic surfactant (an octylphenoxy polyethoxy ethanol sold by Rohm and Haas, Co.). The incubations were continued for about 18 hours at 37° C. The latices were then centrifuged, the supernatants discarded, and the resulting pellets were washed twice with phosphate buffered saline and were resuspended in it.

Two samples of a chloromethylstyrene-derived latex [a core-shell copolymer having a core of poly-(styrene-co-divinylbenzene) (99.2:0.8 molar ratio) and a shell of poly(vinylbenzyl chloride-co-divinylbenzene (98.8:1.2 molar ratio)] (100 mg dry polymer in each sample) were incubated with a 3.16 mg sample of one of the above-described antibodies in 30 ml of 0.1 molar sodium borate buffer at pH of 8.5. The reactions were conducted as described above for the carboxylated latex except that the initial incubation was conducted at 37° C. rather than at room temperature.

The amount of antibody bound to each latex preparation was determined by assaying the number of counts for samples run in parallel having $^3H$ bovine gamma globulin bound to core-shell particles having a core of poly(styrene-co-divinylbenzene) and a shell of poly(-vinylbenzylchloride-co-divinylbenzene) and particles of poly(styrene-co-acrylic acid) by exactly the same procedures, and in the same amounts, as given above. The relative amount of active antibody in each preparation was determined in an assay in which serial dilutions of the latex ($3.16 \times 10^{-10}$ molar to $1 \times 10^{-6}$ molar theoretical theophylline binding sites based on the mass of antibody bound) were mixed with a fixed concentration of a theophylline-glucose oxidase label ($5 \times 10^{-10}$ molar). The latex dilutions and label were incubated for about 1 hour with constant agitation at room temperature in phosphate buffered saline containing 1% bovine serum albumin. The amount of theophylline-glucose oxidase label remaining in solution following centrifugation was determined and the concentration of theophylline binding sites required to bind 50% of the enzyme label was determined. The results are summarized below:

| Mass Binding Experiment: | | |
|---|---|---|
| | % Bound | mg $^3H$ bovine gamma globulin/ g Latex |
| Core-Shell Copolymer Latex | 58.3% | 18.4 |
| Poly(styrene-co-acrylic acid) (99:1 molar ratio) | 54.4% | 17.2 |

| Latex-Enzyme Label Titration: | | |
|---|---|---|
| Latex | Antibody | nmolar Theoretical theophylline binding sites where 50% of the label is bound |
| Core-Shell Copolymer | 1 | 2.1 |
| | 2 | 11.3 |
| Poly(styrene-co-acrylic acid) (99:1 molar ratio) | 1 | 3.6 |
| | 2 | 2.5 |

This example demonstrates that antibody can be covalently bound to carboxylated beads using ambient reaction conditions according to the present invention at approximately the same efficiency as it can be attached to beads via active halogen groups at elevated temperatures. In addition it demonstrates that the antibody can be attached to activated carboxylated beads with the same degree of preservation of antibody activity as is seen with the alternative protocol of direct linking of the antibodies to the polymer bead via active halogen groups. In several previous experiments it has been shown that more than 50% of the mass of antibody attached to active halogen beads by the procedure described herein remain active towards tritiated theophylline. Therefore it is expected that the same would be observed for the antibody attached to activated carboxyl beads.

EXAMPLE 3

Comparison with Carbodiimide Attachment

This example compares the method of the present invention to a method of attaching a protein to a particle using known carbodiimide chemistry, and compares the use of the resulting reagents in an assay for phenobarbital.

A monoclonal antibody to phenobarbital was prepared at Eastman Kodak Co. by immunization of Balb/c mice with a conjugate of phenobarbital-human serum albumin. Spleens of the immunized mice were fused with myeloma (SP2/0-Ag 14) cells to generate the hybridomas. This preparatory method used known procedures.

The antibody so prepared was covalently attached to polymeric particles having pendant carboxyl groups on the outer surfaces. The particles were composed of poly(styrene-co-methacrylic acid) (90:10 molar ratio). The mass of antibody bound to the particles was determined in a parallel experiment in which tritiated bovine gamma globulin was used in place of the anti-phenobarbital antibody. The amount of active protein bound to the particles was compared in the enzyme label binding experiment as described in Example 2 above.

One sample of the polymeric particles described above (30 mg dry weight) was mixed with 1-(4-morpholinocarbonyl)-4-(2-sulfoethyl)pyridinium hydroxide, inner salt (16 mg, 1.5 mmole/g beads) in 10 ml of 0.1 molar 2-(N-morpholino)ethanesulfonic acid buffer (pH 6) for 10 minutes, followed by the addition of the anti-phenobarbital antibody (0.3 mg). A second sample of the polymeric latex was mixed with the same inner salt, followed by addition of 1.5 mg of the anti-phenobarbital antibody.

A third sample of the same latex was mixed with 1-cyclohexyl-3-(2-morpholinoethyl)carbodiimide metho-p-toluenesulfonate (19.1 mg, 1.5 mmole/g beads) for ten minutes, followed by the addition of 0.3 mg of the anti-phenobarbital antibody. A fourth sample of the latex particles was mixed with the carbodiimide, followed by the addition of 1.5 mg of antibody. These samples are identified as Controls 1 and 2 in the tables below.

The attachment reactions were carried out by incubation of the mixtures for 24 hours with end-over-end rotation at room temperature. The reactions were stopped by the addition of bovine serum albumin (30 mg, 30 mg/ml), and incubation was then continued for an additional four hours. The reaction mixtures were centrifuged, the supernatant discarded, and the pellets washed once with phosphate buffered saline solution (pH 7.4), and then resuspended in the saline solution.

The mass of antibody bound to each latex preparation was determined by assaying the number of radioactive counts for samples run in parallel having tritiated bovine gamma globulin bound to the particles as described in Example 1. The covalent/total ratio was calculated following incubation with sodium dodecylsulfate surfactant as described in Example 1. The results of the mass binding experiment are summarized in Tables III and IV below.

The relative amount of active antibody in each preparation was determined in an enzyme label binding experiment similar to the one described in Example 2. The present example demonstrates that the anti-phenobarbital antibody can be covalently bound to the polymeric particles using the carbamoylonium compound at very high efficiency. It also demonstrates that the antibody can be attached to form a useful immunological reagent. At the low antibody/polymer bead ratio, a four-fold lower concentration of immobilized antibody reagent of the present invention was required to bind 50% of the labeled antigen than for the Control reagent (compare 86 nmolar theoretical phenobarbital binding sites of the Control to 19 nmolar for the invention at 0.3 mg protein added). This suggests a four times greater retention of antibody activity for the method of the present invention over the carbodiimide chemistry of the prior art.

TABLE III (Mass Binding Experiment)

| Attachment Method | Labeled Protein Used (mg) | % Bound | mg $^3$H Protein/ g polymer | Covalent/ Total |
|---|---|---|---|---|
| Example 3 | 0.3 | 82.8 | 8.28 | 0.99 |
| Example 3 | 1.5 | 82.8 | 41.4 | 0.93 |
| Control 1 | 0.3 | 90.7 | 9.07 | 0.94 |
| Control 2 | 1.5 | 73.8 | 36.9 | 0.80 |

TABLE IV (Latex-Enzyme Label Titration)

| Attachment Method | Labeled Protein Used (mg) | Theoretical Phenobarbital Binding Sites to Bind 50% of Label (nmolar) |
|---|---|---|
| Example 3 | 0.3 | 19 |
| Example 3 | 1.5 | 10 |
| Control 1 | 0.3 | 86 |
| Control 2 | 1.5 | 10 |

EXAMPLE 4

Attachment of Diamine to Polymeric Particles

This example illustrates the practice of the present invention by the attachment of diamines to carboxylated polymeric particles using a carbamoylonium compound. The importance of this feature of the invention resides in the fact that it is difficult to prepare particles having reactive amine moieties on the outer surface using known polymerization methods of amine-containing monomers.

A portion (3 g dry weight) of poly(styrene-co-acrylic acid)(90:10 molar ratio) suspended in deionized distilled water (100 ml) was combined with 1.5 g of 1-(4-morpholinocarbonyl)-4-(2-sulfoethyl)-pyridinium hydroxide, inner salt dissolved in deionized distilled water (60 ml) and the volume was brought to 300 ml with distilled water. The reaction mixture was stirred at room temperature for 30 minutes, and then centrifuged at 10° C. and 6000 rpm for 30 minutes. The supernatant was discarded, and the beads were resuspended in 90 ml of deionized distilled water. The latex containing thusly activated polymeric particles was divided into three portions and each portion was reacted with an excess of one of the three diamines described below.

Reaction A:

Diamine A, Hexanediamine (567 mg), was dissolved in 30 ml of 0.1 molar sodium borate buffer (pH 8) and the pH was adjusted to 8. This solution was added to 30 ml of the activated latex and the volume was brought to 100 ml with borate buffer.

Reaction B:

Diamine B, L-lysine.1HCl (548 mg), was dissolved and reacted as described for Reaction A.

Reaction C:

Diamine C, L-lysyl-L-lysine.2HCl (260 mg), was also dissolved and reacted as described for Reaction A.

The three reactions described above were continued for four hours at room temperature and end-over-end rotation. Each reaction mixture was then placed in a dialysis bag, and dialyzed against deionized distilled water for about 24 hours. They were then centrifuged for 30 minutes at 6000 rpm and the supernatant was discarded. Each reaction product was then resuspended in 100 ml of deionized distilled water, and the centrifugation and resuspension process repeated twice more. The resulting reaction products contained the respective diamine covalently attached to the latex particles.

Each reaction product prepared above was reacted with an IgG protein having oxidized aldehyde groups in the following manner:

The IgG was first dialyzed into sodium phosphate buffer (0.01 molar, pH 6) containing sodium chloride (0.15 molar). The IgG protein used was tritiated bovine gamma globulin ($^3$H BGG). The carbohydrate of the protein was oxidized with NaIO$_4$ at a final concentration of 30 mmolar for 1 hour at room temperature. Glycerol was added at a final concentration of 100 mmolar to stop the reaction and excess reagents were removed by passage of the reaction through a commercially available Pharmacia PD-10 desalting column using the manufacturer's instructions.

A portion (30 mg dry weight) of each of the three reaction products described above was combined with 1.5 mg of the oxidized protein and brought to a final volume of 9 ml with 0.01 molar sodium phosphate buffer (pH 6) containing 0.15 molar sodium chloride in a 15 ml centrifuge tube. The resulting reactions were continued for five hours at room temperature with end-over-end rotation. A 1 ml solution of NaBH$_3$CN (100 mmolar) was added to each reaction and the rotation was continued for an additional 16 hours at room temperature.

A Control material (Control 1) was similarly prepared by substituting a portion of the original carboxylated latex for the latex containing diamine moieties. Three additional Controls (2–4) were similarly prepared by substituting unoxidized tritiated bovine gamma globulin for the oxidized protein in the reactions with each diamine latex. Unoxidized tritiated bovine gamma globulin was also added to the original carboxylated latex in Control 5.

At the end of the described reactions, each reaction was quenched by the addition of excess bovine serum albumin (30 mg, 30 mg/ml in buffer). The samples were then incubated another four hours after addition of the quenching protein.

The total amount of antibody bound to the latex particles was determined by the procedures described in Example 2 above. The fraction of the $^3$H BGG which is covalently bound to the particles was determined following incubation in the presence of 1% sodium dodecyl sulfate as described in Example 2 above. The results are provided in Table V below.

TABLE V

| Polymeric Reaction Product | IgG | Total Bound (mg BGG/g Polymer) | Covalent Bound (mg BGG/g Polymer) | Covalent/ Total Ratio |
|---|---|---|---|---|
| Invention: | | | | |
| Diamine A | Oxidized | 28 | 20 | 0.71 |
| Diamine B | Oxidized | 29 | 21 | 0.72 |
| Diamine C | Oxidized | 27 | 23 | 0.85 |
| Controls: | | | | |
| Control 1 (No Diamine) | Oxidized | 25 | 11 | 0.44 |
| Control 2 (Diamine A) | Unoxidized | 22 | 1.2 | 0.05 |
| Control 3 (Diamine B) | Unoxidized | 22 | 2.5 | 0.11 |
| Control 4 (Diamine C) | Unoxidized | 21 | 3.9 | 0.19 |
| Control 5 (No Diamine) | Unoxidized | 25 | 1.9 | 0.08 |

These results with Diamines A–C demonstrate that the diamines reacted with the carboxyl groups on the polymeric particles following activation by the carbamoylonium compound according to the present invention. The resulting amine moieties on the particles then reacted with the oxidized aldehyde groups on the tritiated IgG. As shown by the data, aldehyde groups must be present on the protein for substantial binding to the amine moieties on the particles. Where the groups were not oxidized (Controls 2–5), only a small fraction of the protein was covalently attached to the particles. In addition, sufficient amine moieties must be present on the particles for significant covalent attachment. Little covalent attachment is seen with the carboxylated particles alone (Control 1).

The invention has been described in detail with particular reference to preferred embodiments thereof, but it will be understood that variations and modifications can be effected within the spirit and scope of the invention.

We claim:

1. A method for attaching a reactive amine- or sulfhydryl-containing compound to polymeric particles comprising:

A. contacting (1) an aqueous suspension of polymeric particles having pendant carboxyl groups on the surface thereof with (2) a carbamoylonium compound to produce reactive intermediate polymer particles having pendant intermediate reactive groups, and B. contacting the reactive intermediate polymer particles produced in step A with a reactive amine- or sulfhydryl-containing compound having a reactive amine or sulfhydryl group, respectively, which reacts with said intermediate reactive groups to form a covalent linkage between said particles and said reactive compound, wherein said carbamoylonium compound has the structure:

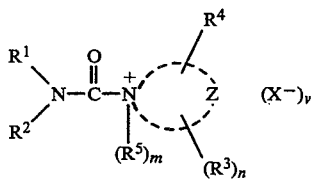

wherein

Z represents the atoms necessary to complete a substituted or unsubstituted 5- or 6-membered heterocyclic aromatic ring, m and n are independently 0 or 1, $R^1$ and $R^2$ are independently of each other, substituted or unsubstituted alkyl, substituted or unsubstituted aryl, or substituted or unsubstituted aralkyl, or $R^1$ and $R^2$ together represent the atoms necessary to complete a substituted or unsubstituted piperidine, piperazine or morpholine ring, $R^3$ is a hydrogen atom, a substituted or unsubstituted alkyl, or the group $+A]$ wherein A represents the polymerized vinyl backbone of a homo- or copolymer formed from one or more ethylenically unsaturated polymerizable compounds such that the molecular weight of said homo- or copolymer is greater than about 1000, $R^4$ is a hydrogen atom, a substituted or unsubstituted alkyl, or when Z represents the atoms necessary to complete a pyridinium ring and n is 0, $R^4$ is selected from the following groups:

(a) —$NR^6$—CO—$R^7$ wherein $R^6$ is hydrogen or substituted or unsubstituted alkyl, $R^7$ is hydrogen, substituted or unsubstituted alkyl or —$NR^8R^9$ wherein $R^8$ and $R^9$ are independently hydrogen or substituted or unsubstituted alkyl, (b) —$(CH_2)_q$—$NR^{10}R^{11}$ wherein $R^{10}$ is —CO—$R^{12}$, $R^{11}$ is hydrogen or substituted or unsubstituted alkyl, $R^{12}$ is hydrogen, substituted or unsubstituted alkyl or —$NR^{13}R^{14}$ wherein $R^{13}$ is substituted or unsubstituted alkyl or substituted or unsubstituted aryl, $R^{14}$ is hydrogen, substituted or unsubstituted alkyl or substituted or unsubstituted aryl, and q is 1 to 3, (c) —$(CH_2)_r$—$CONR^{15}R^{16}$ wherein $R^{15}$ is hydrogen, substituted or unsubstituted alkyl or substituted or unsubstituted aryl, $R^{16}$ is hydrogen or substituted or unsubstituted alkyl, or $R^{15}$ and $R^{16}$ together represent the atoms necessary to complete a 5- or 6-membered aliphatic ring and r is 0 to 3,

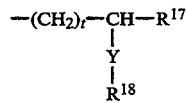

wherein $R^{17}$ is hydrogen, substituted or unsubstituted alkyl, Y is oxy or —$NR^{19}$-, $R^{18}$ is hydrogen, substituted or unsubstituted alkyl, —CO—$R^{20}$ or —CO—$NHR^{21}$ wherein $R^{19}$, $R^{20}$ and $R^{21}$ are independently hydrogen or substituted or unsubstituted alkyl, and t is 2 or 3, and (e) —$R^{21}X'^{\ominus}$ wherein $R^{21}$ is substituted or unsubstituted alkylene, and $X'^{\ominus}$ is a covalently bonded anionic group so as to form an inner salt group with the pyridinium ring, $R^5$ is substituted or unsubstituted alkyl, substituted or unsubstituted aryl or substituted or unsubstituted aralkyl, provided that m is 0 when the nitrogen atom to which $R^5$ is bound is attached to remainder of the ring through a double bond, and X is an anion, and v is 0 or 1, provided that it is 0 only when $R^4$ is $-R^{21}X'^{\ominus}$.

2. The method of claim 1 wherein either said polymeric particles used in step A or said reactive amine- or sulfhydryl-containing compound used in step B has a detectable tracer compound associated therewith.

3. The method of claim 1 wherein said reactive amine- or sulfhydryl-containing compound is a polypeptide or protein.

4. The method of claim 1 wherein said carbamoylonium compound is present in a molar ratio to said carboxyl groups of from about 1:100 to about 10:1.

5. The method of claim 1 wherein the weight ratio of said reactive compound to said polymeric particles is from about 1:1000 to about 1:1.

6. The method of claim 1 carried out at a temperature of from about 10° C. to about 60° C.

7. The method of claim 1 wherein said carbamoylonium compound has the defined structure wherein $R^1$ and $R^2$ together represent the atoms necessary to complete a morpholine ring, Z represents the atoms necessary to complete a pyridinium ring, $R^4$ is $-R^{21}X'^{\ominus}$, and m n and v are each 0.

8. The method of claim 1 wherein said carbamoylonium compound is selected from the group consisting of:

1-(4-morpholinocarbonyl)-4-(2-sulfoethyl)pyridinium hydroxide, inner salt, and 1-(4-morpholinocarbonyl)-pyridinium chloride.

9. The method of claim 1 wherein said carbamoylonium compound is 1-(4-morpholinocarbonyl)-4-(2-sulfoethyl)pyridinium hydroxide, inner salt.

10. The method of claim 1 wherein said polymeric particles are composed of a polymer represented by the structure:

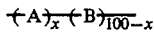

wherein A represents recurring units derived from one or more ethylenically unsaturated polymerizable monomers containing carboxylic acid groups or salts or precursors of said groups, and B represents recurring units derived from one or more ethylenically unsaturated polymerizable monomers, and x is from about 0.1 to about 70 mole percent.

11. The method of claim 10 wherein said polymeric particles are composed of the defined polymer wherein A is derived from acrylic acid, methacrylic acid, iraconic acid, β-carboxyethyl acrylate, β-carboxyethyl methacrylate, m&p-carboxymethylstyrene, methacrylamidohexanoic acid or N-(2-carboxy-1,1-dimethylethyl)acrylamide, or a salt or anhydride precursor thereof, and B is derived from styrene or a styrene derivative, an acrylic or methacrylic acid ester, or acrylonitrile and x is from about 1 to about 20 mole percent.

12. The method of claims 11 wherein said polymeric particles are composed of poly(styrene-co-vinylbenzyl chloride-co-acrylic acid), poly-(styrene-co-acrylic acid), poly(styrene-co-methacrylic acid), poly(styrene-co-acrylic acid-co-m&p-divinylbenzene) or poly(styrene-co-2-carboxyethyl acrylate).

13. The method of claim 1 wherein said polymeric particles have an average particle size of from about 0.01 to about 5 micrometers.

14. The method of claim 1 wherein said polymeric particles are core-shell particles wherein the core is composed of a first polymer and the shell is composed of a second polymer containing carboxylic acid groups or salts or precursors thereof.

15. The method of claim 14 wherein said core-shell polymer particles contain a detectable tracer in the core only.

16. The method of claim 1 wherein said reactive amine- or sulfhydryl-containing compound is an immunologically reactive species.

17. The method of claim 16 wherein said immunologically reactive species is an antibody.

18. The method of claim 17 wherein said antibody is directed to Streptococcus A antigen, a chlamydial antigen, a gonococcal antigen, human chorionic gonadotropin, human leutinizing hormone or a herpes virus.

19. The method of claim 16 wherein said immunologically reactive species is an antibody against a drug or hormone.

20. The method of claim 16 wherein said immunologically reactive species is a HTLV or HIV antigen.

21. A kit comprising: (1) polymeric particles having pendant carboxyl groups on the surface thereof, and (2) a carbamoylonium compound having the structure:

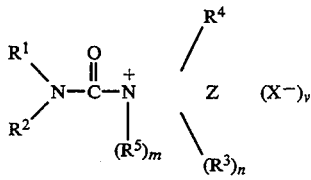

wherein

Z represents the atoms necessary to complete a substituted or unsubstituted 5- or 6-membered heterocyclic aromatic ring, m and n are independently 0 or 1, $R^1$ and $R^2$ are independently of each other, substituted or unsubstituted alkyl, substituted or unsubstituted aryl, or substituted or unsubstituted aralkyl, or $R^1$ and R2 together represent the atoms necessary to complete a substituted or unsubstituted piperidine, piperazine or morpholine ring, $R^3$ is a hydrogen atom, a substituted or unsubstituted alkyl, or the group

+A]

wherein A represents the polymerized vinyl backbone of homo- or copolymer formed from one or more ethylenically unsaturated polymerizable compounds such that the molecular weight of said homo- or copolymer is greater than about 1000, $R^4$ is a hydrogen atom, a substituted or unsubstituted alkyl, or when Z represents the atoms necessary to complete a pyridinium ring and n is 0, $R^4$ is selected from the following groups:

(a) $-NR^6-CO-R^7$ wherein $R^6$ is hydrogen or substituted or unsubstituted alkyl, $R^7$ is hydrogen, substituted or unsubstituted alkyl or $-NR^8R^9$ wherein $R^8$ and $R^9$ are independently hydrogen or substituted or unsubstituted alkyl, (b) $-(CH_2)_q-NR^{10}R^{11}$ wherein $R^{10}$ is $-CO-R^{12}$, $R^{11}$ is hydrogen or substituted or unsubstituted alkyl, $R^{12}$ is hydrogen, substituted or unsubstituted alkyl or $-NR^{13}R^{14}$ wherein $R^{13}$ is substituted or unsubstituted alkyl or substituted or unsubstituted aryl, $R^{14}$ is hydrogen, substituted or unsubstituted alkyl or substituted or unsubstituted aryl, and q is 1 to 3, (c) $-(CH_2)_r-CONR^{15}R^{16}$ wherein $R^{15}$ is hydrogen, substituted or unsubstituted alkyl or substituted or unsubstituted aryl, $R^{16}$ is hydrogen or substituted or unsubstituted alkyl, or $R^{15}$ and $R^{16}$ together represent the atoms necessary to complete a 5- or 6-membered aliphatic ring, and r is 0 to 3, (d)

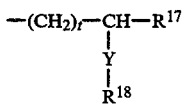

wherein $R^{17}$ is hydrogen, substituted or unsubstituted alkyl, Y is oxy or $-NR^{19}-$, $R^{18}$ is hydrogen, substituted or unsubstituted alkyl, $-CO-R^{20}$ or $,CO-NHR^{21}$ wherein $R^{19}$, $R^{20}$ and $R^{21}$ are independently hydrogen or substituted or unsubstituted alkyl, and t is 2 or 3, and (e) $-R^{21}X'^{\ominus}$ wherein $R^{21}$ is substituted or unsubstituted alkylene, and $X'^{\ominus}$ is a covalently bonded anionic group so as to form an inner salt group with the pyridinium ring, $R^5$ is substituted or unsubstituted alkyl, substituted or unsubstituted aryl or substituted or unsubstituted aralkyl, provided that m is 0 when the nitrogen atom to which $R^5$ is bound is attached to the remainder of the ring through a double bond, and X is an anion and v is 0 or 1, provided that it is 0 only when $R^4$ is $-R^{21}X'^{\ominus}$.

22. The kit of claim 21 wherein said particles have a detectable tracer compound associated therewith.

23. The kit of claim 22 wherein said tracer compound is a colorimetric or fluorometric dye incorporated within the particles.

24. The kit of claim 21 further comprising a compound having a reactive amine or sulfhydryl group for attachment to said particles.

25. The kit of claim 24 wherein said reactive compound is an immunologically reactive species.

26. The kit of claim 21 wherein said polymeric particles are composed of a polymer represented by the structure:

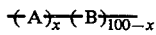

wherein A represents recurring units derived from one or more ethylenically unsaturated polymerizable monomers containing carboxylic acid groups or salts or precursors of said groups, and B represents recurring units derived from one or more ethylenically unsaturated polymerizable monomers, and x is from about 0.1 to about 70 mole percent.

27. The kit of claim 21 wherein said polymeric particles are provided in an aqueous suspension.

* * * * *